US008834390B2

(12) United States Patent
Couvillon, Jr.

(10) Patent No.: US 8,834,390 B2
(45) Date of Patent: *Sep. 16, 2014

(54) ELECTRONICALLY ACTIVATED CAPTURE DEVICE

(75) Inventor: Lucien Alfred Couvillon, Jr., Concord, MA (US)

(73) Assignee: Boston Scientific Scimed, Inc., Maple Grove, CA (US)

( * ) Notice: Subject to any disclaimer, the term of this patent is extended or adjusted under 35 U.S.C. 154(b) by 370 days.

This patent is subject to a terminal disclaimer.

(21) Appl. No.: 12/617,703

(22) Filed: Nov. 12, 2009

(65) Prior Publication Data

US 2010/0056953 A1  Mar. 4, 2010

Related U.S. Application Data

(63) Continuation of application No. 11/454,700, filed on Jun. 16, 2006, now abandoned, which is a continuation of application No. 10/177,838, filed on Jun. 21, 2002, now Pat. No. 7,063,671.

(51) Int. Cl.
| | |
|---|---|
| *A61B 10/00* | (2006.01) |
| *A61B 17/221* | (2006.01) |
| *F03G 7/00* | (2006.01) |
| *A61M 25/00* | (2006.01) |
| *A61B 17/00* | (2006.01) |
| *A61B 17/22* | (2006.01) |

(52) U.S. Cl.
CPC ............... *F03G 7/00* (2013.01); *A61B 17/221* (2013.01); *A61M 2025/0058* (2013.01); *A61B 2017/00871* (2013.01); *F03G 7/005* (2013.01); *A61B 2017/00345* (2013.01); *A61B 2017/2212* (2013.01); *A61B 2017/22034* (2013.01); *A61B 2017/00398* (2013.01)
USPC ............................ 600/564; 600/565; 606/167

(58) Field of Classification Search
USPC .............. 600/562–567; 604/93.1, 102.1, 264, 604/508, 509, 523, 533; 606/110, 114, 115, 606/167
See application file for complete search history.

(56) References Cited

U.S. PATENT DOCUMENTS 4,919,133 A * 4/1990 Chiang ......................... 606/159
5,250,167 A   10/1993 Adolf et al.
(Continued)

FOREIGN PATENT DOCUMENTS

| DE | 2945237 A1 | 5/1981 |
|---|---|---|
| WO | WO 00/78222 A1 | 12/2000 |
| WO | WO 01/58973 A2 | 8/2001 |

OTHER PUBLICATIONS

American Society for Gastrointestinal Endoscopy, "Technology Status Evaluation Report: Endoscopic Retrieval Devices," Dec. 1999, vol. 50, No. 6, pp. 1-5. http://www.asge.org;gui/resources/manual/misc_endo_retrieval_devices.asp.

(Continued)

*Primary Examiner* — Max Hindenburg
*Assistant Examiner* — Jonathan M Foreman
(74) *Attorney, Agent, or Firm* — Kacvinsky Daisak Bluni PLLC (57) ABSTRACT

A novel capture device apparatus comprising: (a) a capture device portion, at least a part of which is adaptable for insertion into a patient and (b) a control unit. The capture device portion comprises one or more apertures and one or more electroactive polymer actuators that open and close the one or more apertures based on control signals sent from the control unit. In another aspect of the present invention, a method of capturing a specimen within a patient's body of provided. The method comprises (a) providing a capture device apparatus like that above, (b) inserting at least a portion of the capture device portion of the apparatus into the patient such that the capture device portion is adjacent the specimen; and (c) closing the one or more apertures using the control unit, thereby capturing the specimen.

21 Claims, 10 Drawing Sheets

(56) References Cited

U.S. PATENT DOCUMENTS

| | | | |
|---|---|---|---|
| 5,268,082 | A | 12/1993 | Oguro et al. |
| 5,339,799 | A | 8/1994 | Kami et al. |
| 5,372,124 | A | 12/1994 | Takayama et al. |
| 5,389,222 | A | 2/1995 | Shahinpoor |
| 5,423,830 | A | 6/1995 | Schneebaum et al. |
| 5,431,645 | A | 7/1995 | Smith et al. |
| 5,556,700 | A | 9/1996 | Kaneto et al. |
| 5,631,040 | A | 5/1997 | Takuchi et al. |
| 5,741,271 | A | 4/1998 | Nakao et al. |
| 5,855,565 | A | 1/1999 | Bar-Cohen et al. |
| 6,109,852 | A | 8/2000 | Shahinpoor et al. |
| 6,249,076 | B1 | 6/2001 | Madden et al. |
| 6,514,237 | B1 | 2/2003 | Maseda |
| 6,749,556 | B2 | 6/2004 | Banik |
| 7,063,671 | B2 * | 6/2006 | Couvillon, Jr. ............ 600/562 |
| 2002/0062062 | A1 | 5/2002 | Belson et al. |
| 2002/0169391 | A1 * | 11/2002 | Hung et al. ............... 600/562 |
| 2003/0229332 | A1 | 12/2003 | Intoccia |

OTHER PUBLICATIONS

*WorldWide ElectroActive Polymers (Artificial Muscles) Newsletter*, Jun. 2001, vol .3, No. 1, pp. 1-14.

Jager, Edwin W.H., et al. Microfabricating Conjugated Polymer Actuators, Science, No. 24, 2000, vol. 290, pp. 1540-1545.

Bar-Cohen, Yoseph, ed., *Electroactive Polymer (EAP) Actuators as Artificial Muscles*, Chap. 16, Roy Kornbluh et al. "Application of Dielectric Elastomer EAP Actuators, " SPIE Press, 2001, pp. 457-495.

Bar-Cohen, Yoseph, ed. *Electroactive Polymer (EAP) Actuators as Artificial Muscles*, Chap. 21, Yoseph Bar-Cohen, "EAP Applications, Potential, and Challenges," SPIE Press, 2001, pp. 615-659.

Bar-Cohen, Yoseph, "Transition of EAP Material from Novelty to Practical Applications—Are We There Yet?" Yoseph Bar-Cohen, ed., *Smart Structures and Materials 2001: Electroactive Polymer Actuators and Devices*, Proceedings of SPIE, vol. 4329, Mar. 5-8, 2001, pp. 1-6.

Madden, John D.W. et al., "Polypyrole Actuators: Modeling and Performance" Yoseph Bar-Cohen, ed., *Smart Structures and Materials 2001: Electroactive Polymer Actuators and Devices*, Proceedings of SPIE, vol. 4329, Mar. 5-8, 2001, pp. 72-83.

Pelrine, Ron et al., "Applications of Dielectric Elastomer Actuators," Yoseph Bar-Cohen, ed., *Smart Structure and Materials 2001 Electroactive Polymer Actuators and Devices*, Proceedings of SPIE, vol. 4329, Mar. 5-8, 2001, pp. 335-349.

Brock, David L., "Review of Artificial Muscle Based on Contractile Polymers," Massachusetts Institute of Technology Artificial Intelligence Laboratory, A.I. Memo No. 1330, Nov. 1991, pp. 1-12. http://www.ai.mit.edu/projects/muscle/papers/memo1330/memo1330.html.

Bar-Cohen, Yoseph, ed., *Electroactive Polymer (EAP) Actuators as Artificial Muscles*, Chap. 7, Jose-Maria Sansinena et al., "Conductive Polymers," SPIE Press, 2001, pp. 193-221.

Bar-Cohen, Yoseph, ed., *Electroactive Polymer (EAP) Actuators as Artificial Muscles*, Chap. 1, Yoseph Bar-Cohen, EAP History, Current Status, and Infrastructure, SPIE Press, 2001, pp. 3-44.

Sansinena et al., Artificial Muscle Preparation Procedure using Polypyrrole and a Solid Polymer Electrolyte, NDEA Group, Jet Propulsion Laboratory, Sep. 19, 2000.

\* cited by examiner

ELECTRONICALLY ACTIVATED CAPTURE DEVICE

STATEMENT OF RELATED APPLICATION

This patent application is a continuation of U.S. patent application Ser. No. 11/454,700, filed Jun. 16, 2006, entitled "Electronically Activated Capture Device," which is a continuation of U.S. patent application Ser. No. 10/177,838, filed Jun. 21, 2002, entitled "Electronically Activated Capture Device," now U.S. Pat. No. 7,063,671, which is related to U.S. Ser. No. 09/971,419, filed Oct. 5, 2001, entitled "Robotic Endoscope," now U.S. Pat. No. 6,835,173. Each of the prior applications is incorporated herein by reference in its entirety.

INTRODUCTION

1. Field of the Invention

The present invention relates to medical devices useful for the capture of a specimen within a patient.

2. Background of the Invention

Capture devices such as polypectomy snares, stone removal snares and baskets, and embolus capture devices, are routinely used in urology, endoscopy, interventional cardiology, and interventional radiology to extract specimens from the body of a patient, for example, to remove a blockage or to provide a biopsy specimen. Typically, long pull-wires are used to actuate a basket, snare or other capture mechanism at a catheter tip. Such mechanisms, however, limit the size, flexibility, and actuation force of the device.

SUMMARY OF THE INVENTION

The present invention provides various advantages over prior art capture devices, which typically rely on pull wire actuators.

According to one aspect of the present invention, a novel capture device apparatus is provided in which electroactive polymer actuators are used to capture a specimen of interest. The capture device apparatus preferably comprises: (a) a capture device portion, at least a part of which is adaptable for insertion into a patient and (b) a control unit. The capture device portion comprises one or more apertures and one or more electroactive polymer actuators that open and close the one or more apertures based on control signals sent from the control unit.

The electroactive polymer actuators beneficially comprise (a) an active member, (b) a counter-electrode and (c) a region comprising an electrolyte disposed between the active member and the counter-electrode. In preferred embodiments, the one or more electroactive polymer actuators further comprise a substrate layer and a barrier layer, with the active member, counter-electrode and the region comprising the electrolyte being disposed between the substrate layer and barrier layer. Preferred electroactive polymers for the practice of the present invention include polyaniline, polypyrrole, polysulfone and polyacetylene.

The one or more apertures within the device capture portion can be mechanically biased, for example, toward either an open position or a closed position.

In some embodiments, the one or more apertures are closed upon contraction of the one or more actuators and opened upon expansion of the one or more actuators. Conversely, in other embodiments, the one or more apertures are opened upon contraction of the one or more actuators and closed upon expansion of the one or more actuators.

In still other embodiments, the one or more apertures are (a) opened upon expansion of a first set of one or more actuators and contraction of a second set of one or more actuators, and (b) closed upon contraction of the first set of actuators and expansion of the second set of actuators.

In some embodiments, the control unit can simply comprise a power source and a switch. In others, the control unit can be more complex, comprising, for example, a computer. The control unit can be coupled to the one or more actuators in a number of ways, for example, via an electrical cable or wireless interface.

According to another aspect of the present invention, a method of capturing a specimen within a patient's body is provided. The method comprises (a) providing a capture device apparatus like that above, (b) inserting at least a portion of the capture device portion of the apparatus into the patient such that the capture device portion is adjacent the specimen; and (c) closing the one or more apertures using the control unit, thereby capturing the specimen.

In some embodiments, at least one aperture within the capture device portion is lined by one or more blades, allowing the specimen to be severed using the blades. In other embodiments, a vacuum is provided within the device capture portion to draw the specimen into the one or more apertures, assisting capture of the specimen.

The capture device apparatus can be inserted, for example, into a body lumen such as those found within the gastrointestinal tract, respiratory tract, vasculature or urinary tract.

Specimens appropriate for removal using the capture device apparatus of the present invention, include polyps (for instance, sessile and pedunculated polyps), stones, emboli, and various biopsy specimens.

One advantage of the present invention is that a wide array of capture devices is provided.

Another advantage of the present invention is that compact capture devices are provided which are capable of exerting very large actuation forces.

These and other embodiments and advantages of the present invention will become apparent to those of ordinary skill in the art based on the following detailed description and the accompanying drawings, which illustrate by way of example the features of the invention.

DETAILED DESCRIPTION OF THE INVENTION

The present invention now will be described more fully hereinafter with reference to the accompanying drawings, in which preferred embodiments of the present invention are shown. This invention may, however, be embodied in different forms and should not be construed as limited to the embodiments set forth herein.

According to preferred embodiments of the present invention, capture devices for insertion into the body of a patient are provided, which contain one or more electroactive polymer actuators. The devices of the present invention can be used to capture a wide array of specimens within the body, for example, emboli, polyps (including polyps of the respiratory tract, cervix and colon), stones (including stones of the liver, gallbladder, and urinary tract), and various biopsy specimens. Patients include vertebrate patients, especially human patients.

Actuators based on electroactive polymers, members of a family of plastics referred to as "conducting polymers," have a number of advantageous attributes, including small size, large force and strain, low cost and ease of integration into the capture devices of the present invention.

Electroactive polymers are a class of polymers characterized by their ability to change shape in response to electrical stimulation. They typically structurally feature a conjugated backbone and have the ability to increase electrical conductivity under oxidation or reduction. Some common electroactive polymers are polyaniline, polysulfone, polypyrrole and polyacetylene. Polypyrrole is pictured below:

These materials are typically semi-conductors in their pure form. However, upon oxidation or reduction of the polymer, conductivity is increased. The oxidation or reduction leads to a charge imbalance that, in turn, results in a flow of ions into the material in order to balance charge. These ions, or dopants, enter the polymer from an ionically conductive electrolyte medium that is coupled to the polymer surface. The electrolyte may be, for example, a gel, a solid, or a liquid. If ions are already present in the polymer when it is oxidized or reduced, they may exit the polymer.

It is well known that dimensional changes may be effectuated in certain conducting polymers by the mass transfer of ions into or out of the polymer. For example, in some conducting polymers, the expansion is due to ion insertion between chains, whereas in others interchain repulsion is the dominant effect. Thus, the mass transfer of ions both into and out of the material leads to an expansion or contraction of the polymer.

Currently, linear and volumetric dimensional changes on the order of 25% are possible. The stress arising from the dimensional change can be on the order of 3 MPa, far exceeding that exerted by smooth muscle cells.

Figure 1:
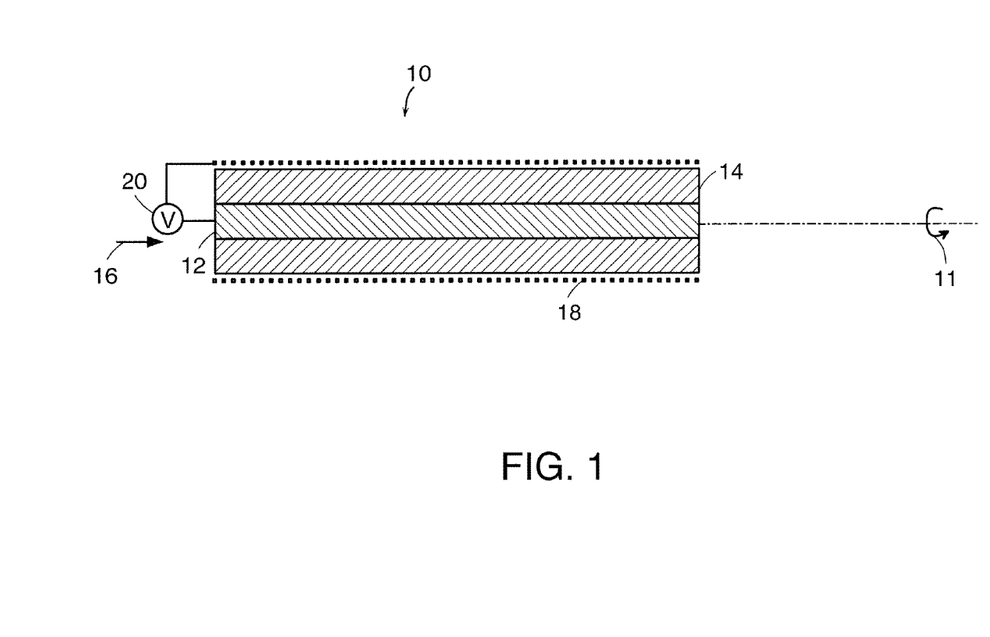
FIG. 1 is a schematic cross-sectional diagram of an actuator useful in connection with the present invention.

Referring now to FIG. 1, an actuator 10 is shown schematically in cross-section. Active member 12 of actuator 10 has a surface coupled with electrolyte 14 and has an axis 11. Active member 12 includes an electroactive polymer that contracts or expands in response to the flow of ions out of, or into, the active member 12. Ions are provided by electrolyte 14, which adjoins member 12 over at least a portion, and up to the entirety, of the surface of active member 12 in order to allow for the flow of ions between the two media. Many geometries are available for the relative disposition of member 12 and electrolyte 14. In accordance with preferred embodiments of the invention, member 12 may be a film, a fiber or a group of fibers, or a combination of multiple films and fibers disposed so as to act in consort for applying a tensile force in a longitudinal direction substantially along axis 11. The fibers may be bundled or distributed within the electrolyte 14.

Active member 12 includes an electroactive polymer. Many electroactive polymers having desirable tensile properties are known to persons skilled in the art. In accordance with preferred embodiments of the invention, active member 12 is a polypyrrole film. Such a polypyrrole film may be synthesized by electrodeposition according to the method described by M. Yamaura et al., "Enhancement of Electrical Conductivity of Polypyrrole Film by Stretching: Counter-ion Effect," Synthetic Metals, vol. 36, pp. 209-224 (1988), which is incorporated herein by reference. In addition to polypyrrole, any conducting polymer that exhibits contractile or expansile properties may be used within the scope of the invention. Polyaniline is an example of such a usable conducting polymer.

Electrolyte 14 may be, for example, a liquid, a gel, or a solid, so long as ion movement is allowed. Moreover, where the electrolyte 14 is a solid, it should move with the active member 12 and should not be subject to delamination. Where the electrolyte 14 is a gel, it may be, for example, an agar or polymethylmethacrylate (PMMA) gel containing a salt dopant. Where the electrolyte is a liquid, it may be, for example, a phosphate buffer solution. The electrolyte is preferably non-toxic in the event that a leak occurs in vivo.

Counter-electrode 18 is in electrical contact with electrolyte 14 in order to provide a return path for charge to a source 20 of potential difference between member 12 and electrolyte 14. Counter-electrode 18 may be any electrical conductor, for example, another conducting polymer, a conducting polymer gel, or a metal such as gold or platinum, which can be applied by electroplating, chemical deposition, or printing, for example. In order to activate actuator 10, a current is passed between active member 12 and counter-electrode 18, inducing contraction or expansion of member 12. Additionally, the actuator may have a flexible skin for separating the electrolyte from an ambient environment.

The actuators can be provided in an essentially infinite array of configurations as desired, including planar actuator configurations, cylindrical actuator configurations (e.g., see the actuator illustrated in FIG. 1), and so forth.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72-83), both of which are hereby incorporated by reference in their entirety.

Actuators can be disposed within the capture devices of the present invention in numerous ways. For example, the actuators can be separately manufactured and subsequently attached to structural elements of the capture devices. As another example, multiple actuators or actuator arrays can be disposed upon a substrate layer, for example, a polymeric sheet, which is associated with the capture device.

Figure 2A:
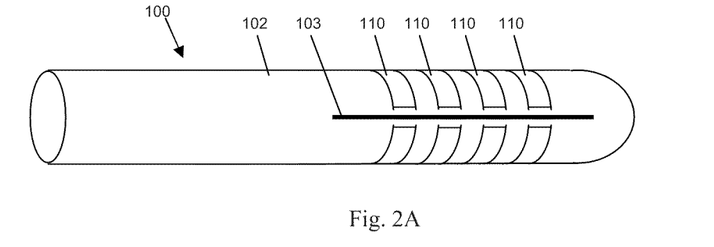
FIGS. 2A and 2B are schematic perspective views of the distal end of a capture device in accordance with an embodiment the present invention, in which an aperture associated with the capture device is illustrated in closed and open positions, respectively.

As a specific example, FIG. 2A illustrates the distal end of a capture device 100 in accordance with an embodiment of the present invention. FIG. 2A illustrates one possible configuration of actuators and structural elements in accordance with the present invention, it being understood, for example, that the number of actuators and structural elements, as well as the spatial disposition of these actuators and elements with respect to one another, can vary widely from one embodiment to another.

The capture device 100 of FIG. 2A contains four actuators 110 and a tubular structural element 102 with aperture 103. The structural element 102 in this embodiment is elastic, while at the same time having sufficient stiffness to allow the device to be advanced into a body lumen. For example, a relatively thick layer of an elastic polymeric material can be used for this purpose as can a polymer material containing one or more stiffening members, for example, thin nitinol stiffening reeds.

In the embodiment of FIG. 2A, the aperture 103 is a simple slit, which is formed in structural element 102. The electroactive polymer actuators 110 are laid out in a fashion that is consistent with the local deformation needed to open the aperture 103. In this example, the actuators are wrapped around the tubular structural element 102. The aperture 103 remains closed so long as the actuators 110 are in an expanded state.

Figure 2B:
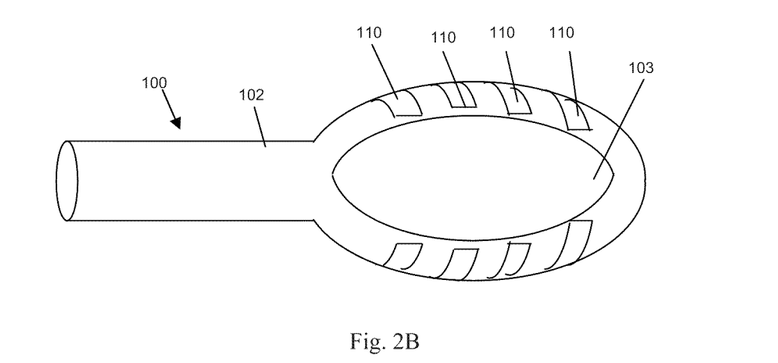

Referring now to FIG. 2B, once the actuators 110 are placed in a contracted state, the aperture 103 in the elastic structural element 102 opens. Once opened, the resultant "mouth" can be used to engulf numerous objects within the body, including polyps, stones, and emboli, as well as various other blockages or specimens. Subsequently, when the actuators 110 are once again placed in an extended state, the aperture 103 returns to the configuration of a slit (due, for example, to the elastic restoring force inherent in structural element 102), capturing the object of interest.

Figure 3:
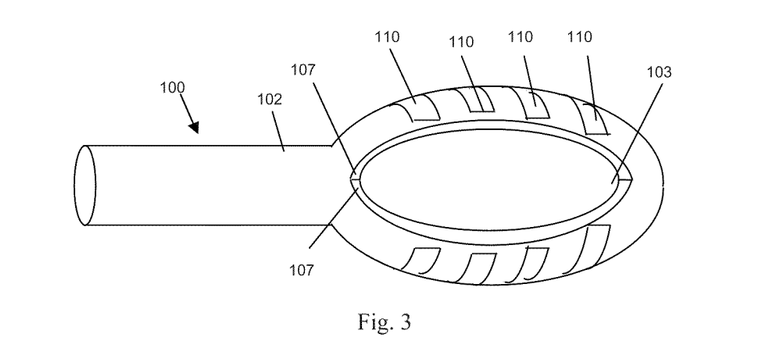
FIGS. 3 and 4 are schematic perspective views of the distal ends of capture devices in accordance with alternative embodiments of the present invention.

Of course, numerous flexible tubular structural elements are known besides the structural element 102 of FIGS. 2A and 2B. For example, rather than being provided in the shape of a solid tube (notwithstanding the aperture), the structural element can be formed using a non-solid flexible tube. Exemplary non-solid flexible tubes include tubular open-mesh networks comprising one or more knitted, woven or braided filaments as well as flexible perforated tubes (e.g., laser-cut tubes). Preferred materials for the tubular structure element 102 are polymeric materials, metallic materials and combinations thereof. For example, a polymeric material reinforced with a braided wire tube, axial stiffening members, or a perforated tube can be used. Reinforced structures of this type are common, for instance, in the guide catheter art.

Where the capture devices of the present invention are employed in operations requiring a cutting step (for example, in the removal of gastrointestinal polyps), it may be desirable to provide the aperture with a cutting edge. For example, it may be possible to sharpen the material defining the edges of the aperture, for instance, where the material is a metal or a hard plastic material. Alternatively, as illustrated in FIG. 3, the aperture can be provided with blades 107 of flexible metal material. Suitable blades include blades of the type presently used in connection with Boston Scientific's Cutting Balloon™ Device (for more information, see, e.g., http://www.bostonscientific.com).

Figure 4:
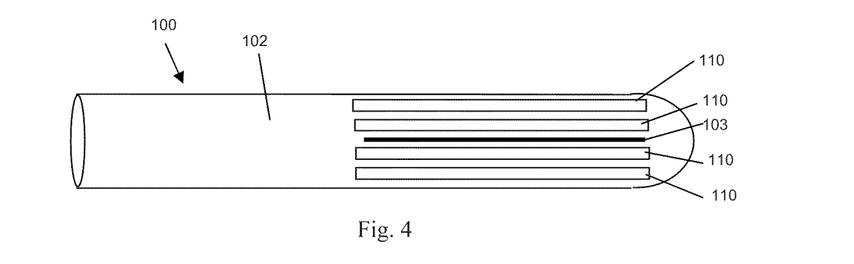

In the above embodiments, the actuators are wrapped around a portion of the circumference of the tubular structural element 102. However, numerous additional configurations are possible. For example, referring now to FIG. 4, a capture device 100 is illustrated containing elastic tubular structural element 102 with aperture 103. Four electroactive polymer actuators 110 are disposed on the surface of tubular structural element 102 and are oriented in a direction that is coaxial with the tubular element 102. Combinations of actuator orientations are also possible. For example, actuators having a circumferential orientation like that of FIG. 2A can be combined with actuators having a co-axial orientation, like that of FIG. 4.

In the above embodiments, the actuators are used to open the device aperture to allow capture of a specimen of interest, while the closing force is provided by the inherent elasticity of the structural element. In other embodiments, the actuators are used to close the apertures, with the opening force being inherent in the structural element.

Figure 5A:
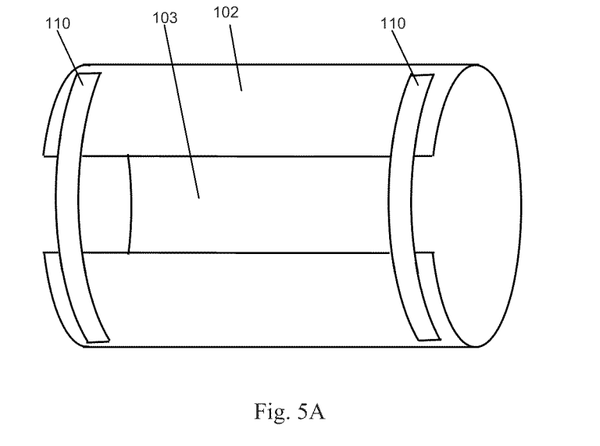
FIGS. 5A and 5B are schematic perspective views of a capture mechanism for use in a capture device in accordance with an embodiment of the present invention, in which an aperture associated with the capture mechanism is illustrated in closed and open positions, respectively.
Figure 5B:
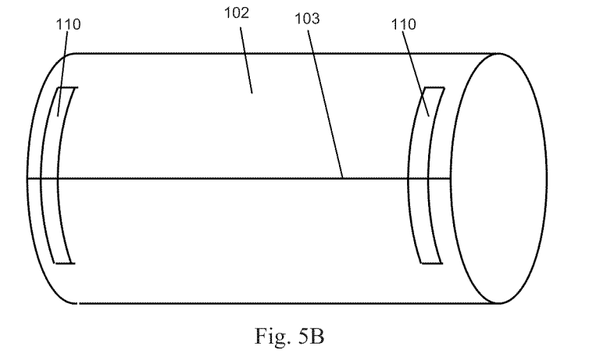

For example, referring now to FIG. 5A, a cylindrical structural element 102 is illustrated. Two electroactive polymer actuators 110 are attached to the structural element 102. The structural element 102 of FIG. 5A contains an aperture 103 which remains open so long as the actuators 110 are in an extended state. Upon contraction of the actuators 110, however, the aperture 103 closes as illustrated in FIG. 5B. When the actuators 110 are returned to an extended state, the elasticity inherent in the structural member 102 opens the aperture 103 once again. Where the structural element is a hard plastic or metal, for example, stainless steel, the edges adjacent the aperture 103 can be sharpened as discussed above.

Figure 6:
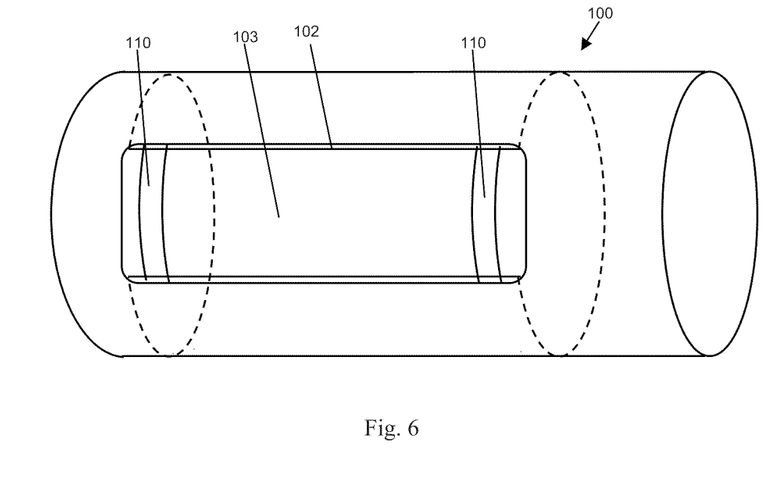
FIG. 6 is a schematic perspective view of the capture mechanism of FIG. 5A, upon being disposed within the distal end of a capture device in accordance with an embodiment of the present invention.

A structure likes that of FIGS. 5A-B can be readily incorporated into the distal end of a capture device 100 as illustrated in FIG. 6.

In alternative designs, multiple actuators can be placed in opposition with one another to achieve the desired shape. For example, referring now to FIG. 7A there is illustrated a cross-sectional view of the distal end of a capture device 100, which includes a stiff inner tubular member 106, such as a stainless steel or nitinol tube, and a flexible outer jacket 104, such as a polyurethane jacket, having multiple slits (see FIGS. 8A and 8B below). Actuators 110a and 110b are attached to both the jacket 104 and stiff tubular member 106 via adhesive regions 119. The jacket 104 is preferably adhered to the stiff tubular member 106 at the distal end of the device, but the jacket 104 is otherwise axially movable along stiff tubular member 106.

Figure 7A:
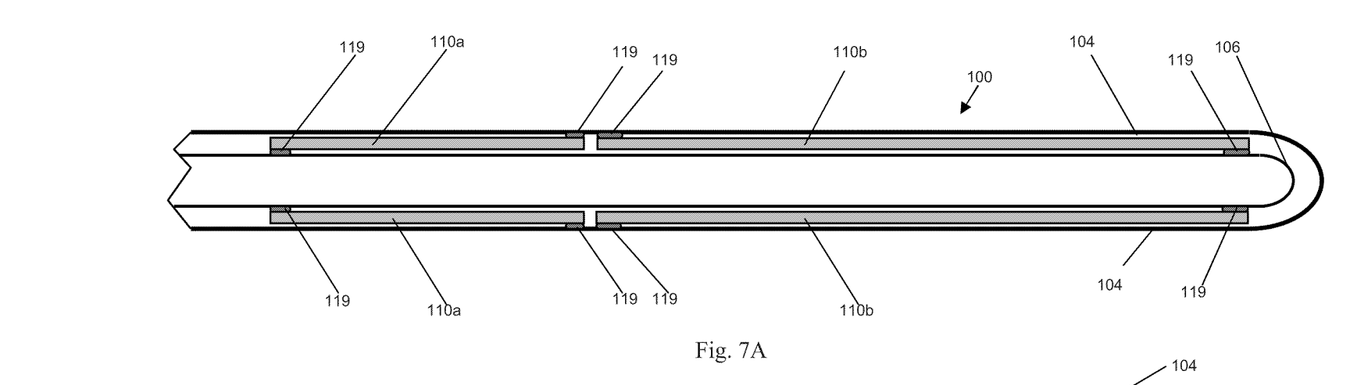
FIGS. 7A and 7B are cross-sectional views of the distal end of a capture device in accordance with an embodiment the present invention, in closed and open positions, respectively.

In the configuration illustrated in FIG. 7A, actuators 110a are in a contracted state, while actuators 110b are in an expanded state. Because the jacket 104 is attached to the rigid tubular member 106 at the end of rigid tubular member 106 and because these components are otherwise axially movable relative to one another, upon the expansion of actuators 110a and the contraction of actuators 110b, the jacket 104 buckles in the region outside of actuators 110b as illustrated in FIG. 7B.

Figure 8A:
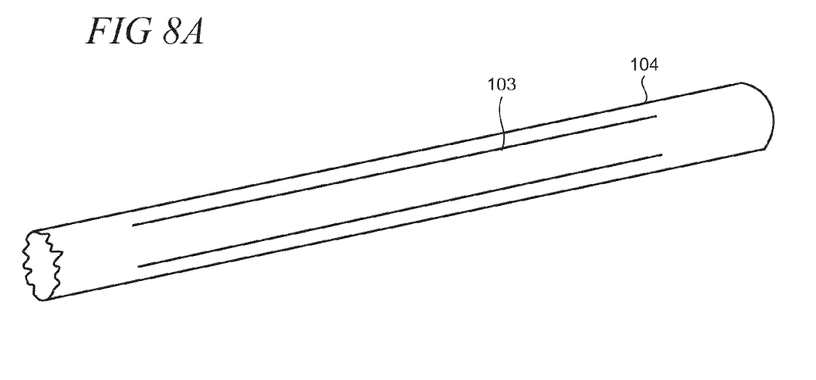
FIGS. 8A and 8B are schematic perspective views of the outer jacket portion of the distal end of a capture device like that of FIGS. 7A and 7B, in which apertures associated with the outer jacket are illustrated in closed and open positions, respectively.
Figure 8B:
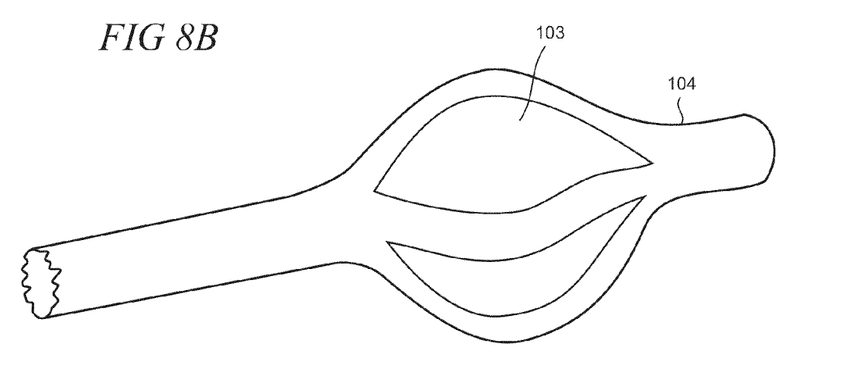

The effect of buckling the outer jacket 104 can be better seen in FIGS. 8A and 8B. Due to presence of slits 103 in jacket 104 (see FIG. 8A), upon buckling of the jacket, the slits 103 widen, forming capture apertures (see FIG. 8B).

Figure 7B:
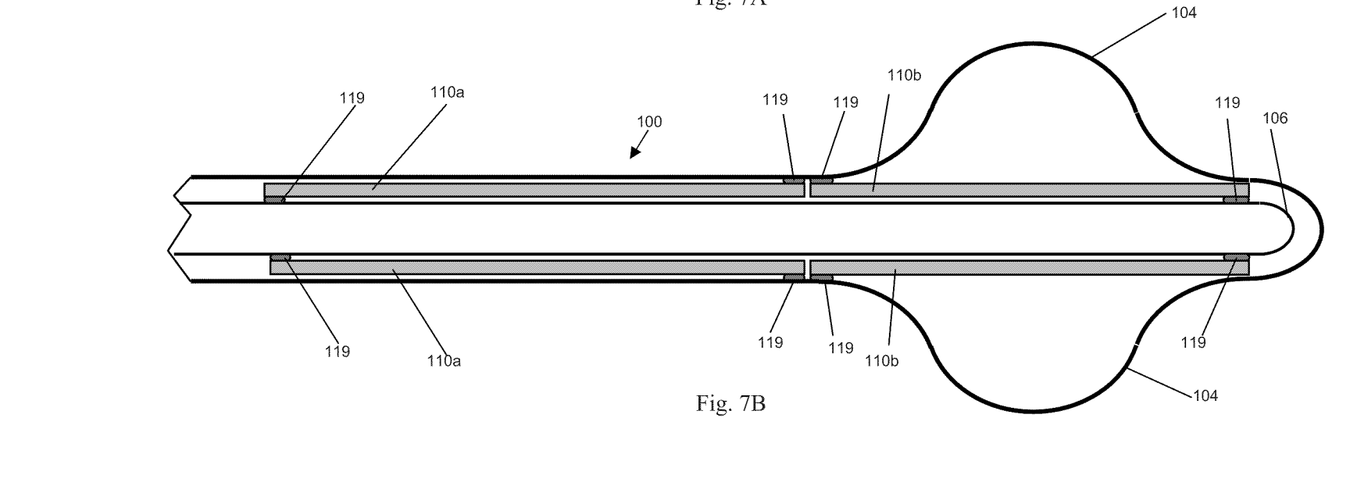

Hence, in the capture device of FIGS. 7A-B, opening and closing forces are exerted by two sets of opposing actuators. This eliminates the need for an inherent mechanical bias to provide the necessary force to open or close the device. The same is true for the device of FIGS. 7C-D immediately below.

Figure 7C:
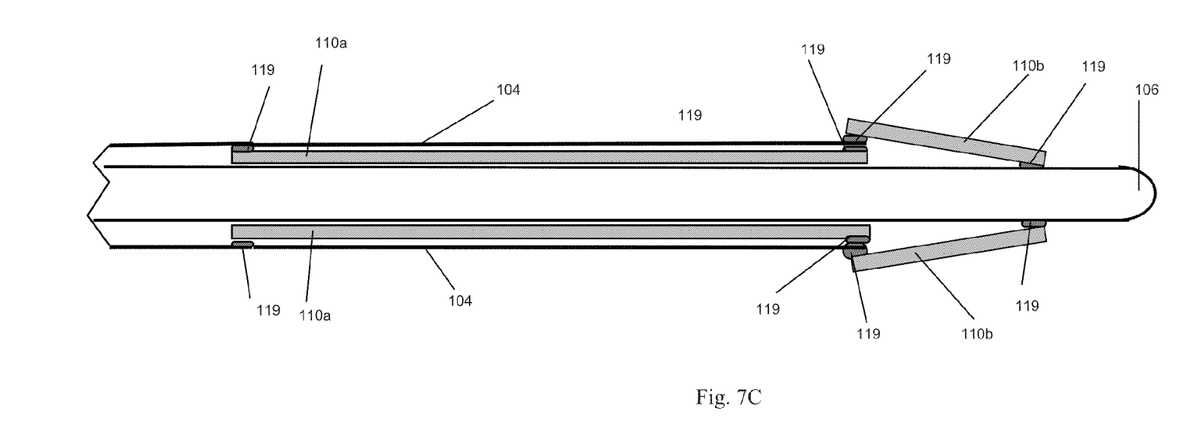
FIGS. 7C and 7D are cross-sectional views of the distal end of a capture device in accordance with another embodiment the present invention, in closed and open positions, respectively.
Figure 7D:
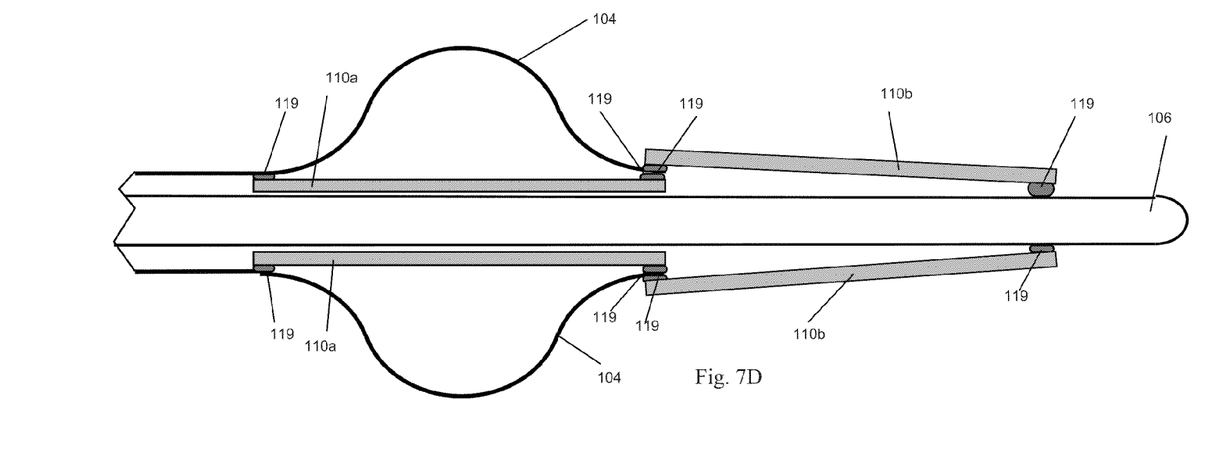

A variation of the design of FIGS. 7A-B is illustrated in FIGS. 7C-D. Referring now to FIG. 7C, there is illustrated a cross-sectional view of the distal end of a capture device 100, which includes a stiff inner tubular member 106 and a flexible outer jacket 104. Actuators 110a are attached to the jacket 104, while actuators 110b are attached to both the jacket 104 and the stiff tubular member 106, via adhesive regions 119.

In the configuration illustrated in FIG. 7C, actuators 110a are in an expanded state, while actuators 110b are in a contracted state. Upon contraction of actuators 110a and expansion of actuators 110b as illustrated in FIG. 7D, the jacket 104 buckles in the region outside of actuators 110a in a manner similar to the above.

In general, the orientation of the aperture(s) in the capture devices of the present invention can be inferred from the intrinsic position-dependent electrical properties of the electroactive polymer actuators therein. However, strain gauges can be employed to provide electronic feedback concerning the orientation of the actuators and openings within the assembly, if desired. This electronic feedback will also provide a number of additional advantages, including greater stability, error correction, and immunity from drift. Electronic feedback also permits a haptic interface to the controller, in which the operator may "feel" the force fed back. Strain gauges suitable for use in the present invention include (a) feedback electroactive polymer elements whose impedance or resistance varies as a function of the amount of strain in the device and (b) conventional strain gauges in which the resistance of the device varies as a function of the amount of strain in the device, thus allowing the amount of strain to be readily quantified and monitored. Such strain gauges are commercially available from a number of different sources, including National Instruments Co., Austin, Tex., and include piezoresistive strain gauges (for which resistance varies nonlinearly with strain) and bonded metallic strain gauges (for which resistance typically varies linearly with strain).

Feedback regarding the capture device configuration, as well as the relationship between the capture device and the body into which it is inserted (including the specimen which is sought for capture), may also be obtained using conventional medical imaging techniques, including radiographic contrast dye techniques, fluoroscopy, ultrasound imaging, MR imaging, computed tomography, visual endoscopy, and other well known modalities of image-guided surgery.

The actuators within the capture devices of the present invention can be individually controlled or controlled as a group. Where individual control is desired, the actuators (and strain gauges, if desired) may be placed in direct communication with a controlling device by means of dedicated circuits linking each of these elements to the device. On the other hand, these elements can also be deployed in an array in which each element is in communication with the controlling device by means of a common communications cable. The signals from each element may be digital or analog. If need be, digital-to-analog or analog-to-digital converters may be provided to convert the signals from one format to the other. The signals to and from each element may be conveniently managed and transmitted over a common cable by multiplexing.

Figure 9A:
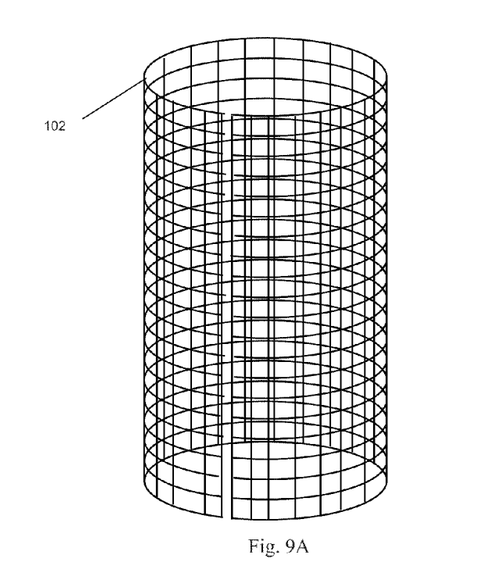
FIG. 9A is a schematic perspective view of a structural element for use in a capture device, in accordance with an embodiment of the present invention.
Figure 9B:
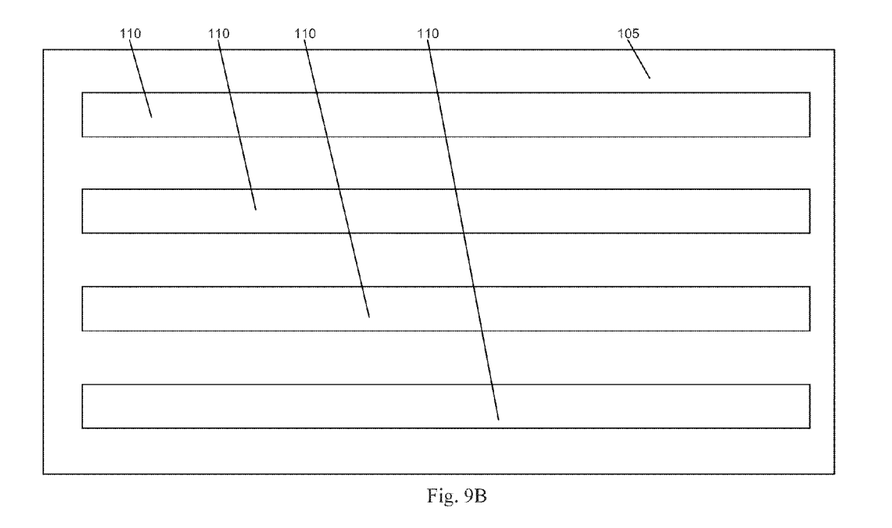
FIG. 9B is a schematic perspective view of a substrate layer with attached electroactive polymer actuators, in accordance with an embodiment of the present invention.
Figure 9C:
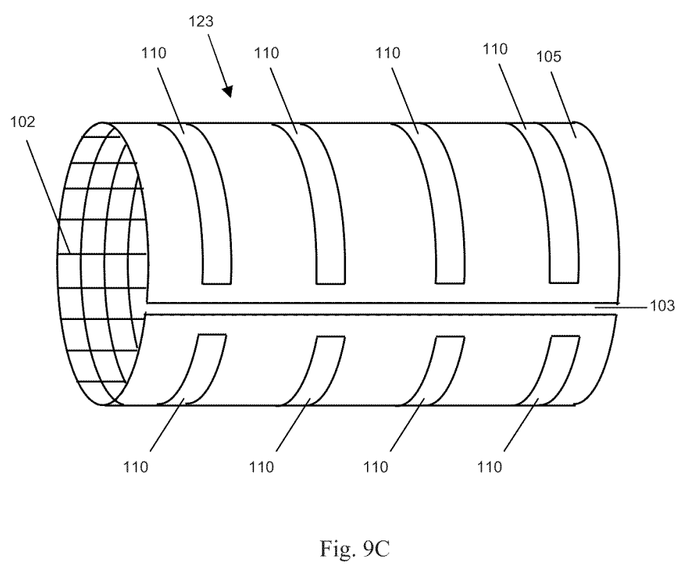
FIG. 9C is a schematic perspective view of the structural element of FIG. 9A upon being wrapped in the substrate layer of FIG. 9B, in accordance with an embodiment of the present invention.

In many preferred embodiments, the actuators are provided on a substrate layer, which is subsequently incorporated into the capture device. For example, FIGS. 9A-C illustrate a structural element 102, which is a braided wire tube analog of the structural element 102 of FIG. 5A. The structural element 102 of FIG. 9A, however, is inherently biased to a position in which the slot is closed. (If desired, ends can be provided on wire tube 102 to provide an enclosed wire basket structure.) FIG. 9B illustrates four actuators 110 attached on the surface of substrate layer 105, along with a control bus (not shown), which can be, for example, track wires for transmitting control signals to the actuators 110 from a controlling device.

The substrate layer 105 with attached actuators 110 of FIG. 9B is wrapped around the structural element 102 of FIG. 9A, providing a cylindrical assembly 123 as illustrated in FIG. 9C. Cylindrical assembly 123 is then incorporated into the distal end of a capture device, whereupon contraction of the actuator elements 110 results in an enlargement of aperture 103, while expansion of the actuator elements 110 results in closure of aperture 103.

It is noted that the device of FIGS. 9A-9C uses actuator contraction to open the aperture of the device, while relying on the inherent bias of the structural element to effect device closure. However, if desired, additional actuators can be provided, for example, along the lines of the device of FIGS. 5A-5B, to provide a device in which both closing and opening forces are exerted by two sets of actuators in opposition with one another. In this case, the need for an inherent bias within the structural element to effect device closure is eliminated.

Although FIGS. 9A-9C illustrate a single substrate layer 105, multiple substrate layers can be used. As one example, an additional substrate layer can be provided which contains strain gauges, such as feedback polymer elements, along with a readout bus for transmitting information from the strain gauges to a controlling device. As another example, multiple actuator layers can be employed.

Actuators 110 can be provided on substrate layer 105 in numerous configurations. For example, a single actuator 110 is shown in cross-section in FIG. 10A, disposed on substrate layer 105. As previously discussed, the actuator 110 includes an active member 112 as a first electrode along with a counter-electrode 118, with an intervening electrolyte-containing layer 114.

Figure 10A:
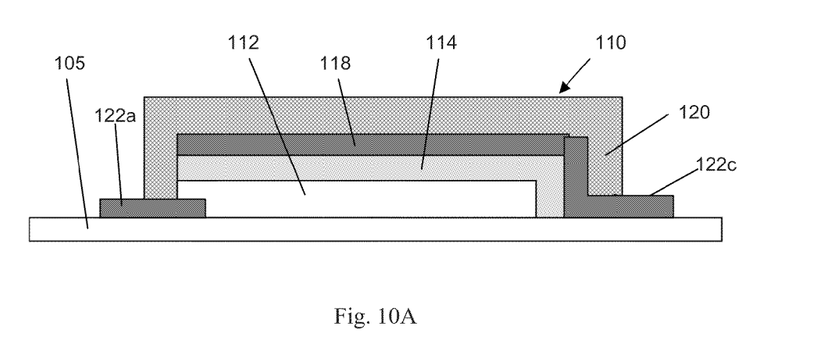
FIGS. 10A-10C are schematic cross sectional views illustrating actuator configurations, in accordance with three embodiments of the present invention.

The substrate layer 105 is formed of a flexible material. Electrically insulating materials are preferred. Flexible materials useful in the construction of the substrate layer 105 include the following polymeric materials: polyolefins such as metallocene catalyzed polyethylenes, polypropylenes, and polybutylenes and copolymers thereof; ethylenic polymers such as polystyrene; ethylenic copolymers such as ethylene vinyl acetate (EVA), butadiene-styrene copolymers and copolymers of ethylene with acrylic acid or methacrylic acid; polyacetals; chloropolymers such as polyvinylchloride (PVC); fluoropolymers such as polytetrafluoroethylene (PTFE); polyesters such as polyethylene terephthalate (PET); polyester-ethers; polysulfones; polyamides such as nylon 6 and nylon 6,6; polyamide ethers such as polyether block amides; polyethers; elastomers such as elastomeric polyurethanes and polyurethane copolymers; silicones; polycarbonates; polychloroprene; nitrile rubber; butyl rubber; polysulfide rubber; cis-1,4-polyisoprene; ethylene propylene terpolymers; as well as mixtures and block or random copolymers of any of the foregoing are non-limiting examples of biostable polymers useful for manufacturing the medical devices of the present invention.

In some embodiments, the substrate layers are constructed from stiff polymers like those used in electronic printed circuits or cables, such as polyimide (e.g., Kapton®), and relieved by selective cutting, e.g. with a laser, to provide the appropriate flexibility.

The active member 112 of FIG. 10A comprises an electroactive polymer, many of which are known in the art as discussed above. Polypyrrole, polysulfone and polyaniline are three specific examples.

The counter-electrode 118 may be any electrical conductor, for example, another conducting polymer or a metal such as gold or platinum, preferably in a flexible form, for example, in the form of a thin layer or foil, which can be applied by electroplating, chemical deposition, or printing, for example.

The electrolyte within the electrolyte-containing layer 114 can be, for example, a liquid, a gel, or a solid as previously discussed. In the embodiment illustrated, contact between the active member 112 and counter-electrode 118 is prevented by providing the electrolyte within a flexible porous layer of insulating polymer material. Beneficial insulating polymers for this purpose include insulating polymers within the polymer list provided above in connection the substrate layer 105. PTFE is a specific example.

Thin track wires 122a and 122c are connected to active member 112 and counter-electrode 118, respectively, allowing for electrical communication with a controlling device (not shown).

Barrier layer 120 is provided for several reasons. For example, the barrier layer 120 prevents species within the electrolyte-containing layer 114 from escaping. Appropriate materials for the barrier layer include those discussed above in connection with substrate layer 105.

Figure 10B:
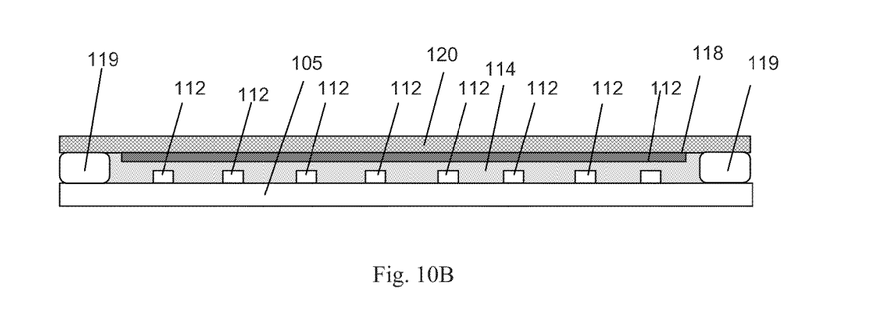

Numerous actuator configurations other than that illustrated in FIG. 10A are also possible. For example, FIG. 10B is a cross-section illustrating eight active members 112 disposed on substrate layer 105. Over the active members are electrolyte-containing layer 114, counter-electrode layer 118, and barrier layer 120. The barrier layer 120 is sealed to the substrate layer 105 using, for example, an adhesive region 119. The configuration of FIG. 10B contains a common counter-electrode. The active members 112, on the other hand, are provided with discrete track wires (not shown), allowing for individual or concerted activation, as desired.

Figure 10C:
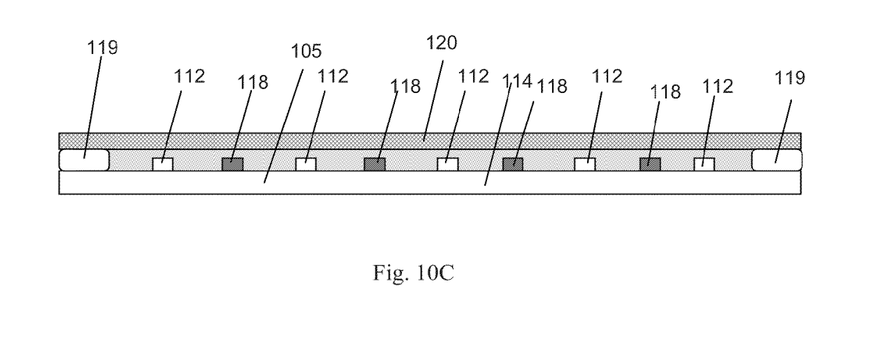

As another example, FIG. 10C is a cross-section including five active members 112 and four counter-electrode regions 118 disposed on a substrate layer 105. An electrolyte-containing layer 114 contacts both the active members 112 and counter-electrode regions 118. A barrier layer 120 is sealed to the substrate layer 105 using, for example, an adhesive 119. The active members 112 are provided with discrete track wires (not shown), allowing individual or concerted activation, as desired. The counter-electrode regions 118 can also be provided with discrete track wires (not shown), or these regions can constitute parts of a single counter-electrode.

As previously noted, substrate layer 105 is formed from an insulating material in many preferred embodiments. However, where the active elements are to be simultaneously actuated, then the substrate layer 105 can be formed form a conductive material, for example, a metal such as gold or platinum. In this instance, the substrate can be used as a current path, eliminating the need for independent track wires.

Figure 11A:
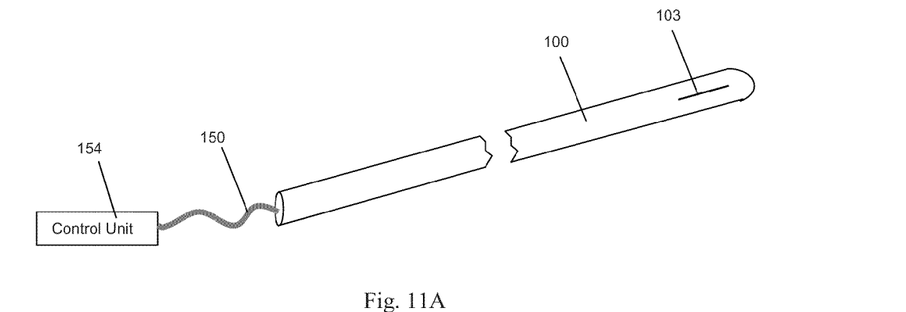
FIGS. 11A-11C are schematic perspective views of capture device apparatuses, in accordance with three embodiments of the present invention.

FIG. 11A is a simplified schematic diagram of a capture device apparatus in accordance with an embodiment of the invention. The capture device apparatus includes a capture device portion 100 containing an aperture 103 and various electronic actuators (not shown), which are controlled by a controlling device 154. An electrical cable 150 is provided between the capture device portion 100 and controlling device 154.

A wide range of controlling devices can be used with the present invention. For example, the controlling device can simply consist of a switch and a power source, such as a battery. Alternatively, the controlling device can be significantly more sophisticated, which is desirable, for example, where individual actuator control is required. As a specific example, a computer provided with an electronic interface (including drivers) can be employed as a controlling device 154. In this instance, signals are sent from drivers in the electronic interface associated with the personal computer 154, through cable bundle 150, to the actuators within capture device portion 100, to open and close the capture device portion 100 as needed.

As noted above, in some embodiments of the invention, the capture device portion 100 is provided with strain gauges, in which case signals are output from the strain gauges and sent via the cable 150 to the electronic interface within controlling device 154. These signals are processed within controlling device 154, for example, to provide feedback regarding the state of the actuators.

Numerous variations are possible. As an example, although the capture device portion 100 and controlling device 154 are illustrated as separate units in the device of FIG. 11A, it is possible to integrate the controlling device into the capture device portion. For example, the controlling device can be integrated into a capture device portion control handle similar to that discussed below.

Figure 11B:
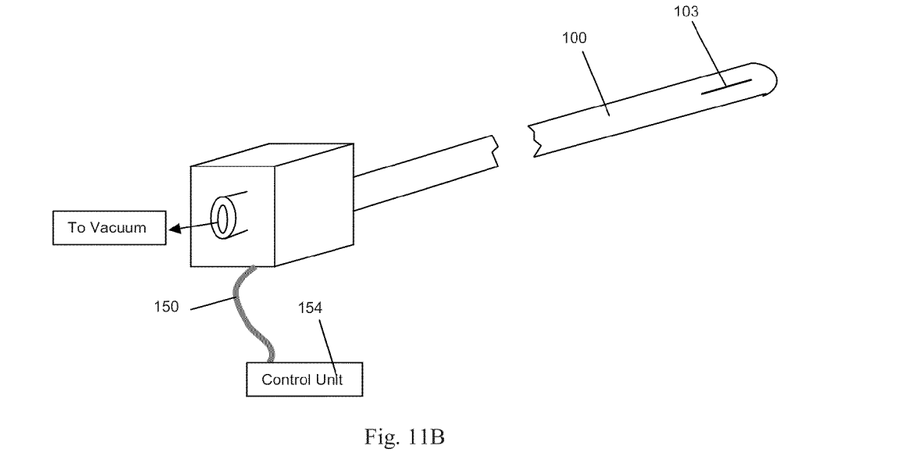

As another example, the body of the capture device portion 100 can contain a channel leading to a vacuum system as illustrated in FIG. 11B, enhancing the ability of the capture device portion to draw a specimen of interest into its aperture 103. For instance, polyps can generally be classified as sessile (broad-based) and pedunculated (on a narrow stalk), with the former being more difficult to remove. However, by applying a vacuum to the capture device portion 100, a sessile polyp can be drawn into the aperture, after which the aperture is closed, cutting off the polyp.

Figure 11C:
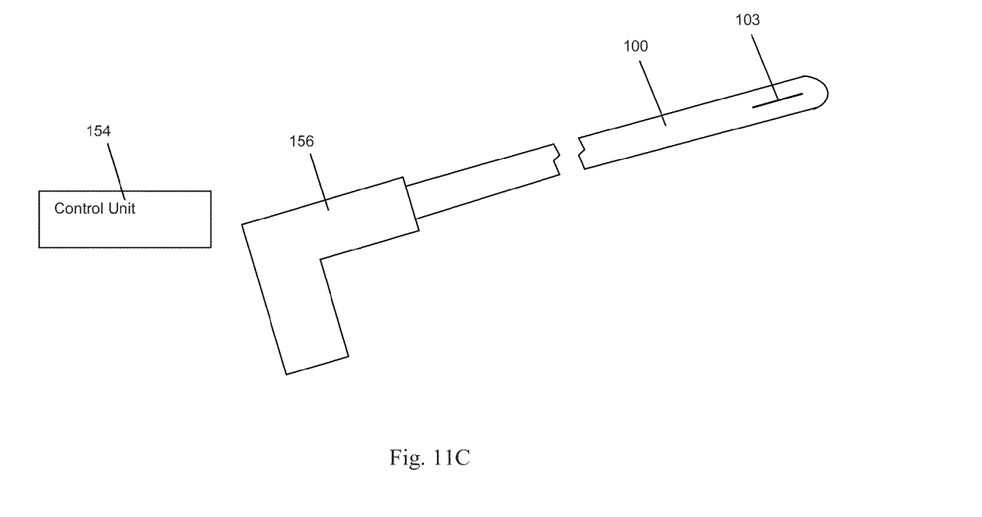

Another example is illustrated in FIG. 11C, in which the capture device apparatus is a wireless system, eliminating the need for a cable 150 like that illustrated in FIGS. 11A-B. For example, a power source, such as a battery can be provided essentially anywhere within the capture device portion 110, but is preferably provided at the proximal end of the capture device portion 100, which can be, for example, in the form of an integrated, sealed control handle 156. The electronics for a wireless interface, including drivers for the electronic actuators and other components, are also preferably provided at the proximal end of the capture device portion 100. At the same time a companion wireless interface is provided within control device 154. Inexpensive wireless interfaces are presently available from a number of sources, including Bluetooth™ wireless interfaces available from Motorola and IEEE 802.11b wireless interfaces available, for example, from Cisco, Apple and Lucent.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. A capture device apparatus for capturing a specimen or specimens from the body of a patient, comprising:
   a capture device portion that comprises:
   (a) a hollow structural element having a hollow interior, at least a part of which is adaptable for insertion into a patient; and
   (b) one or more apertures formed in a sidewall of said hollow structural element; and
   (c) one or more electroactive polymer actuators, wherein, in response to received control signals, said one or more actuators open or close the one or more apertures by locally deforming at least two portions of the sidewall in which the one or more apertures are formed with respect to one another.

2. The capture device apparatus of claim 1, wherein said one or more electroactive polymer actuators comprise an electroactive polymer selected from the group consisting of polyaniline, polypyrrole, polysulfone and polyacetylene.

3. The capture device apparatus of claim 1, wherein the one or more apertures are positioned along a portion of the hollow structural element.

4. The capture device apparatus of claim 1, wherein the hollow structural element is a tubular structural element and said one or more apertures are positioned along a circumferential portion of the hollow structural element.

5. The capture device apparatus of claim 1, wherein the hollow structural element is a tubular structural element and at least one of said one or more apertures are oriented in a direction that is coaxial with the tubular structural element.

6. The capture device apparatus of claim 1, wherein the one or more apertures comprise a plurality of apertures and the hollow structural element is a tubular structural element, at least one of said plurality of apertures being oriented in a direction that is coaxial with the tubular structural element and at least another of said plurality of apertures being positioned along a circumferential portion of the tubular structural element.

7. The capture device apparatus of claim 1, wherein said one or more electroactive polymer actuators further comprise a substrate layer and a barrier layer, and wherein the active member, the counter-electrode and the region comprising the electrolyte are disposed between the substrate layer and barrier layer.

8. The capture device apparatus of claim 7, further comprising conductive lines disposed on said substrate layer.

9. The capture device apparatus of claim 1, wherein said capture device portion further comprises one or more strain gauges.

10. The capture device apparatus of claim 1, wherein said one or more apertures within said device capture portion are mechanically biased toward an open position.

11. The capture device apparatus of claim 1, wherein said one or more apertures within said device capture portion are mechanically biased toward a closed position.

12. The capture device apparatus of claim 1, wherein said one or more apertures are closed upon contraction of said one or more actuators and opened upon expansion of said one or more actuators.

13. The capture device apparatus of claim 1, wherein said one or more apertures are opened upon contraction of said one or more actuators and closed upon expansion of said one or more actuators.

14. The capture device apparatus of claim 1, wherein said one or more apertures are opened upon expansion of a first set of said one or more actuators and contraction of a second set of said one or more actuators, and wherein said one or more apertures are closed upon contraction of said first set and expansion of said second set.

15. The capture device apparatus of claim 1, wherein at least one of said one or more apertures is lined by one or more blades.

16. The capture device apparatus of claim 1, further comprising a vacuum pump coupled to at least one of said one or more apertures.

17. The capture device apparatus of claim 1, wherein said one or more apertures comprise a single slit in said hollow structural element.

18. The capture device apparatus of claim 1, wherein said one or more apertures comprise a plurality of slits in said hollow structural element.

19. The capture device apparatus of claim 1 wherein the hollow interior is inaccessible from the exterior of the capture device portion when said one or more apertures is in a closed position.

20. The capture device apparatus of claim 1 wherein the hollow structural element is substantially free of electroactive polymer material.

21. The capture device apparatus of claim 1, wherein the one or more apertures are opened or closed by elasticity inherent in the sidewall.

* * * * *